(12) United States Patent
Augarten et al.

(10) Patent No.: US 8,698,373 B2
(45) Date of Patent: Apr. 15, 2014

(54) PARE PIEZO POWER WITH ENERGY RECOVERY

(75) Inventors: Mike Augarten, Goleta, CA (US); Sean Snow, Goleta, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 706 days.

(21) Appl. No.: 12/896,148

(22) Filed: Oct. 1, 2010

(65) Prior Publication Data

US 2012/0046520 A1 Feb. 23, 2012

Related U.S. Application Data

(63) Continuation-in-part of application No. 12/859,196, filed on Aug. 18, 2010.

(51) Int. Cl.
*H01L 41/04* (2006.01)

(52) U.S. Cl.
USPC .................................................. 310/316.03

(58) Field of Classification Search
CPC ........................... F02D 41/2096; F02D 41/221
USPC .................................................. 310/314–319
See application file for complete search history.

(56) References Cited

U.S. PATENT DOCUMENTS

| | | |
|---|---|---|
| 2,163,048 A | 6/1939 | McKee |
| 3,667,081 A | 6/1972 | Burger |
| 3,840,018 A | 10/1974 | Heifetz |
| 4,118,805 A | 10/1978 | Reimels |
| 4,157,713 A | 6/1979 | Clarey |
| 4,340,083 A | 7/1982 | Cummins |
| 4,406,656 A | 9/1983 | Hattler et al. |
| 4,450,375 A | 5/1984 | Siegal |
| 4,592,339 A | 6/1986 | Kuzmak et al. |
| 4,592,355 A | 6/1986 | Antebi |
| 4,601,713 A | 7/1986 | Fuqua |
| 4,671,351 A | 6/1987 | Rappe |
| 4,696,288 A | 9/1987 | Kuzmak et al. |
| 4,743,789 A * | 5/1988 | Puskas ..................... 310/316.01 |
| 4,760,837 A | 8/1988 | Petit |
| 4,881,939 A | 11/1989 | Newman |

(Continued)

FOREIGN PATENT DOCUMENTS

| | | |
|---|---|---|
| CN | 1250382 | 4/2000 |
| CN | 1367670 | 9/2002 |

(Continued)

OTHER PUBLICATIONS

Corno et al.; "A new implantable device for telemetric control of pulmonary blood flow," New Ideas; received Apr. 24, 2004; received in revised form Jul. 12, 2002; accepted Jul. 22, 2002.

(Continued)

*Primary Examiner* — Thomas Dougherty
(74) *Attorney, Agent, or Firm* — Gordon & Jacobson, PC

(57) ABSTRACT

The present invention generally relates to medical systems and apparatus and uses thereof for treating obesity and/or obesity-related diseases, and more specifically, relates to systems and methods for energy recovery in a laparoscopically-placed gastric banding system operably coupled to a piezo actuator. The energy recovery may be obtained utilizing an energy recovery device, such as an inductor, coupled to the piezo actuator. The energy recovery device may utilize two circuits to facilitate energy recovery, and the two circuits may include diodes with opposite orientations to control current flow.

20 Claims, 10 Drawing Sheets

(56) References Cited

U.S. PATENT DOCUMENTS

| | | |
|---|---|---|
| 4,883,467 A | 11/1989 | Franetzki et al. |
| 4,944,659 A | 7/1990 | Labbe |
| 5,045,060 A | 9/1991 | Melsky et al. |
| 5,074,868 A | 12/1991 | Kuzmak |
| 5,089,019 A | 2/1992 | Grandjean |
| 5,120,313 A | 6/1992 | Elftman |
| 5,160,338 A | 11/1992 | Vincent |
| 5,226,429 A | 7/1993 | Kuzmak |
| 5,259,399 A | 11/1993 | Brown |
| 5,326,349 A | 7/1994 | Baraff |
| 5,343,894 A | 9/1994 | Frisch et al. |
| 5,360,445 A | 11/1994 | Goldowsky |
| 5,449,368 A | 9/1995 | Kuzmak |
| 5,458,568 A | 10/1995 | Racchini et al. |
| 5,496,312 A | 3/1996 | Klicek |
| 5,535,752 A | 7/1996 | Halperin et al. |
| 5,554,113 A | 9/1996 | Novak et al. |
| 5,562,714 A | 10/1996 | Grevious |
| 5,601,604 A | 2/1997 | Vincent |
| 5,658,298 A | 8/1997 | Vincent et al. |
| 5,676,162 A | 10/1997 | Larson, Jr. et al. |
| 5,733,257 A | 3/1998 | Sternby |
| 5,748,200 A | 5/1998 | Funahashi |
| 5,759,015 A | 6/1998 | Van Lintel et al. |
| 5,766,232 A | 6/1998 | Grevious et al. |
| 5,807,311 A | 9/1998 | Palestrant |
| 5,861,014 A | 1/1999 | Familoni |
| RE36,176 E | 3/1999 | Kuzmak |
| 5,910,149 A | 6/1999 | Kuzmak |
| 5,938,669 A | 8/1999 | Klaiber et al. |
| 6,024,340 A | 2/2000 | Lazarus et al. |
| 6,024,704 A | 2/2000 | Meador et al. |
| 6,042,345 A | 3/2000 | Bishop et al. |
| 6,067,991 A | 5/2000 | Forsell |
| 6,074,341 A | 6/2000 | Anderson et al. |
| 6,083,249 A | 7/2000 | Familoni |
| 6,102,922 A | 8/2000 | Jakobsson et al. |
| 6,164,933 A | 12/2000 | Tani et al. |
| 6,210,347 B1 | 4/2001 | Forsell |
| 6,221,024 B1 | 4/2001 | Miesel |
| 6,306,088 B1 | 10/2001 | Krausman et al. |
| 6,327,503 B1 | 12/2001 | Familoni |
| 6,417,750 B1 | 7/2002 | Sohn |
| 6,432,040 B1 | 8/2002 | Meah |
| 6,439,539 B1 | 8/2002 | Powell |
| 6,450,173 B1 | 9/2002 | Forsell |
| 6,450,946 B1 | 9/2002 | Forsell |
| 6,450,987 B1 | 9/2002 | Kramer |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,454,785 B2 | 9/2002 | De Hoyos Garza |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,475,136 B1 | 11/2002 | Forsell |
| 6,511,490 B2 | 1/2003 | Robert |
| 6,527,701 B1 | 3/2003 | Sayet et al. |
| 6,547,801 B1 | 4/2003 | Dargent et al. |
| 6,579,301 B1 | 6/2003 | Bales et al. |
| 6,676,674 B1 | 1/2004 | Dudai |
| 6,681,135 B1 | 1/2004 | Davis et al. |
| 6,685,668 B1 | 2/2004 | Cho et al. |
| 6,691,047 B1 | 2/2004 | Fredricks |
| 6,715,731 B1 | 4/2004 | Post et al. |
| 6,729,600 B2 | 5/2004 | Mattes et al. |
| 6,754,527 B2 | 6/2004 | Stroebel et al. |
| 6,811,136 B2 | 11/2004 | Eberhardt et al. |
| 6,820,651 B2 | 11/2004 | Seuret et al. |
| 6,834,201 B2 | 12/2004 | Gillies et al. |
| 6,871,090 B1 | 3/2005 | He et al. |
| 6,889,086 B2 | 5/2005 | Mass et al. |
| 6,940,467 B2 | 9/2005 | Fisher et al. |
| 6,966,875 B1 | 11/2005 | Longobardi |
| 7,017,583 B2 | 3/2006 | Forsell |
| 7,017,883 B2 | 3/2006 | Bayer et al. |
| 7,019,436 B2 * | 3/2006 | Rueger et al. ............ 310/316.03 |
| 7,021,147 B1 | 4/2006 | Subramanian et al. |
| 7,037,344 B2 | 5/2006 | Kagan et al. |
| 7,040,349 B2 | 5/2006 | Moler et al. |
| 7,048,519 B2 | 5/2006 | Fong et al. |
| 7,058,434 B2 | 6/2006 | Wang et al. |
| 7,060,080 B2 | 6/2006 | Bachmann |
| 7,066,486 B2 | 6/2006 | Birk |
| 7,118,526 B2 | 10/2006 | Egle |
| 7,128,750 B1 | 10/2006 | Stergiopulos |
| 7,191,007 B2 | 3/2007 | Desai et al. |
| 7,198,250 B2 | 4/2007 | East |
| 7,204,821 B1 | 4/2007 | Clare et al. |
| 7,206,637 B2 | 4/2007 | Salo |
| 7,238,191 B2 | 7/2007 | Bachmann |
| 7,282,023 B2 | 10/2007 | Frering |
| 7,284,966 B2 | 10/2007 | Xu et al. |
| 7,288,064 B2 | 10/2007 | Boustani et al. |
| 7,310,557 B2 | 12/2007 | Maschino et al. |
| 7,311,503 B2 | 12/2007 | Van Lintel et al. |
| 7,311,716 B2 | 12/2007 | Byrum |
| 7,311,717 B2 | 12/2007 | Egle |
| 7,314,443 B2 | 1/2008 | Jordan et al. |
| 7,338,433 B2 | 3/2008 | Coe |
| 7,351,198 B2 | 4/2008 | Byrum et al. |
| 7,351,240 B2 | 4/2008 | Hassler, Jr. et al. |
| 7,353,747 B2 | 4/2008 | Swayze et al. |
| 7,364,542 B2 | 4/2008 | Jambor et al. |
| 7,366,571 B2 | 4/2008 | Armstrong |
| 7,367,340 B2 | 5/2008 | Nelson et al. |
| 7,367,937 B2 | 5/2008 | Jambor et al. |
| 7,374,565 B2 | 5/2008 | Hassler, Jr. et al. |
| 7,390,294 B2 | 6/2008 | Hassler, Jr. |
| 7,396,353 B2 | 7/2008 | Lorenzen et al. |
| 7,416,528 B2 | 8/2008 | Crawford et al. |
| 7,481,763 B2 | 1/2009 | Hassler et al. |
| 7,500,944 B2 | 3/2009 | Byrum et al. |
| 7,530,943 B2 | 5/2009 | Lechner |
| 7,594,885 B2 | 9/2009 | Byrum |
| 7,599,743 B2 | 10/2009 | Hassler, Jr. et al. |
| 7,599,744 B2 | 10/2009 | Giordano et al. |
| 7,601,162 B2 | 10/2009 | Hassler, Jr. et al. |
| 7,615,001 B2 | 11/2009 | Jambor et al. |
| 7,618,365 B2 | 11/2009 | Jambor et al. |
| 7,658,196 B2 | 2/2010 | Ferreri et al. |
| 7,699,770 B2 | 4/2010 | Hassler, Jr. et al. |
| 7,727,141 B2 | 6/2010 | Hassler, Jr. et al. |
| 7,758,493 B2 | 7/2010 | Gingras |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,794,386 B2 | 9/2010 | Brooks |
| 7,811,298 B2 | 10/2010 | Birk |
| 7,844,342 B2 | 11/2010 | Dlugos et al. |
| 2001/0011543 A1 | 8/2001 | Forsell |
| 2002/0072780 A1 | 6/2002 | Foley |
| 2002/0091395 A1 | 7/2002 | Gabbay |
| 2002/0095181 A1 | 7/2002 | Beyar |
| 2002/0139208 A1 | 10/2002 | Yatskov |
| 2002/0193679 A1 | 12/2002 | Malave et al. |
| 2002/0198548 A1 | 12/2002 | Robert |
| 2003/0019498 A1 | 1/2003 | Forsell |
| 2003/0045775 A1 | 3/2003 | Forsell |
| 2003/0055311 A1 | 3/2003 | Neukermans et al. |
| 2003/0066536 A1 | 4/2003 | Forsell |
| 2003/0073880 A1 | 4/2003 | Polsky et al. |
| 2003/0158569 A1 | 8/2003 | Wazne |
| 2003/0191433 A1 | 10/2003 | Prentiss |
| 2003/0208212 A1 | 11/2003 | Cigaina |
| 2004/0000843 A1 | 1/2004 | East |
| 2004/0044332 A1 | 3/2004 | Stergiopulos |
| 2004/0059393 A1 | 3/2004 | Policker et al. |
| 2004/0133219 A1 | 7/2004 | Forsell |
| 2004/0147816 A1 | 7/2004 | Policker et al. |

(56) References Cited

U.S. PATENT DOCUMENTS

| | | |
|---|---|---|
| 2004/0148034 A1 | 7/2004 | Kagan et al. |
| 2004/0153106 A1 | 8/2004 | Dudai |
| 2004/0162595 A1 | 8/2004 | Foley |
| 2004/0215159 A1 | 10/2004 | Forsell |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0002984 A1 | 1/2005 | Byrum et al. |
| 2005/0038484 A1 | 2/2005 | Knudson et al. |
| 2005/0055039 A1 | 3/2005 | Burnett et al. |
| 2005/0070934 A1 | 3/2005 | Tanaka et al. |
| 2005/0070937 A1 | 3/2005 | Jambor et al. |
| 2005/0104457 A1 | 5/2005 | Jordan et al. |
| 2005/0119672 A1 | 6/2005 | Benchetrit |
| 2005/0119674 A1 | 6/2005 | Gingras |
| 2005/0131383 A1 | 6/2005 | Chen et al. |
| 2005/0131485 A1 | 6/2005 | Knudson et al. |
| 2005/0143765 A1 | 6/2005 | Bachmann et al. |
| 2005/0143766 A1 | 6/2005 | Bachmann et al. |
| 2005/0183730 A1 | 8/2005 | Byrum |
| 2005/0192531 A1 | 9/2005 | Birk |
| 2005/0192601 A1 | 9/2005 | Demarais |
| 2005/0192614 A1 | 9/2005 | Binmoeller |
| 2005/0216042 A1 | 9/2005 | Gertner |
| 2005/0228415 A1 | 10/2005 | Gertner |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neill |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler |
| 2005/0267500 A1 | 12/2005 | Hassler et al. |
| 2005/0267533 A1 | 12/2005 | Gertner |
| 2005/0277899 A1 | 12/2005 | Conlon et al. |
| 2005/0283041 A1 | 12/2005 | Egle |
| 2005/0288739 A1 | 12/2005 | Hassler |
| 2005/0288740 A1 | 12/2005 | Hassler |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0089571 A1 | 4/2006 | Gertner |
| 2006/0161186 A1 | 7/2006 | Hassler, Jr. et al. |
| 2006/0173238 A1 | 8/2006 | Starkebaum |
| 2006/0173424 A1 | 8/2006 | Conlon |
| 2006/0178555 A1 | 8/2006 | Bortolotti |
| 2006/0183967 A1 | 8/2006 | Lechner |
| 2006/0189887 A1 | 8/2006 | Hassler et al. |
| 2006/0189888 A1 | 8/2006 | Hassler et al. |
| 2006/0189889 A1 | 8/2006 | Gertner |
| 2006/0195139 A1 | 8/2006 | Gertner |
| 2006/0197412 A1 | 9/2006 | Rasmussen |
| 2006/0199997 A1 | 9/2006 | Hassler et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0212053 A1 | 9/2006 | Gertner |
| 2006/0235448 A1 | 10/2006 | Roslin et al. |
| 2006/0247722 A1 | 11/2006 | Maschino et al. |
| 2006/0247724 A1 | 11/2006 | Gerber et al. |
| 2006/0252982 A1 | 11/2006 | Hassler, Jr. et al. |
| 2006/0264699 A1 | 11/2006 | Gertner |
| 2006/0276812 A1 | 12/2006 | Hill et al. |
| 2007/0015954 A1 | 1/2007 | Dlugos |
| 2007/0015955 A1 | 1/2007 | Tsonton |
| 2007/0016262 A1 | 1/2007 | Gross et al. |
| 2007/0027356 A1 | 2/2007 | Ortiz |
| 2007/0078476 A1 | 4/2007 | Hull et al. |
| 2007/0125826 A1 | 6/2007 | Shelton |
| 2007/0156013 A1 | 7/2007 | Birk |
| 2007/0167672 A1 | 7/2007 | Dlugos et al. |
| 2007/0185462 A1 | 8/2007 | Byrum |
| 2007/0218083 A1 | 9/2007 | Brooks |
| 2007/0232848 A1 | 10/2007 | Forsell |
| 2007/0235083 A1 | 10/2007 | Dlugos |
| 2007/0250085 A1 | 10/2007 | Bachmann et al. |
| 2007/0250086 A1 | 10/2007 | Wiley et al. |
| 2007/0255336 A1 | 11/2007 | Herbert et al. |
| 2007/0265598 A1 | 11/2007 | Karasik |
| 2007/0265645 A1 | 11/2007 | Birk et al. |
| 2008/0009680 A1 | 1/2008 | Hassler, Jr. |
| 2008/0015406 A1 | 1/2008 | Dlugos et al. |
| 2008/0027469 A1 | 1/2008 | Bachmann |
| 2008/0097496 A1 | 4/2008 | Chang et al. |
| 2008/0108862 A1 | 5/2008 | Jordan et al. |
| 2008/0166028 A1 | 7/2008 | Turek et al. |
| 2008/0221598 A1 | 9/2008 | Dlugos et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0319435 A1 | 12/2008 | Rioux et al. |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0204141 A1 | 8/2009 | Dlugos, Jr. et al. |
| 2009/0204179 A1 | 8/2009 | Dlugos, Jr. et al. |
| 2009/0209995 A1 | 8/2009 | Byrum et al. |
| 2009/0216255 A1 | 8/2009 | Coe et al. |
| 2009/0222031 A1 | 9/2009 | Axelsson |
| 2009/0222065 A1 | 9/2009 | Dlugos, Jr. et al. |
| 2009/0228072 A1 | 9/2009 | Coe et al. |
| 2009/0270904 A1 | 10/2009 | Birk et al. |
| 2009/0306462 A1 | 12/2009 | Lechner |
| 2009/0312785 A1 | 12/2009 | Stone et al. |
| 2010/0010291 A1 | 1/2010 | Birk et al. |
| 2010/0087843 A1 | 4/2010 | Bertolote et al. |
| 2010/0099945 A1 | 4/2010 | Birk et al. |
| 2010/0100079 A1 | 4/2010 | Berkcan |
| 2010/0152532 A1 | 6/2010 | Marcotte |
| 2010/0185049 A1 | 7/2010 | Birk et al. |
| 2010/0191271 A1 | 7/2010 | Lau et al. |
| 2010/0228080 A1 | 9/2010 | Tavori et al. |
| 2010/0249803 A1 | 9/2010 | Griffiths |
| 2010/0280310 A1 | 11/2010 | Raven |
| 2010/0305397 A1 | 12/2010 | Birk et al. |
| 2010/0324358 A1 | 12/2010 | Birk et al. |
| 2010/0324359 A1 | 12/2010 | Birk |

FOREIGN PATENT DOCUMENTS

| | | |
|---|---|---|
| DE | 4225524 | 2/1994 |
| DE | 10020688 | 12/2000 |

(56) References Cited

FOREIGN PATENT DOCUMENTS

| | | |
|---|---|---|
| EP | 0119596 | 9/1984 |
| EP | 0230747 | 8/1987 |
| EP | 0611561 | 8/1994 |
| EP | 0695558 | 2/1996 |
| EP | 0867808 | 11/1998 |
| EP | 1072282 | 1/2001 |
| EP | 1396242 | 3/2004 |
| EP | 1396243 | 3/2004 |
| EP | 1491167 | 12/2004 |
| EP | 1547549 | 6/2005 |
| EP | 1600183 | 11/2005 |
| EP | 1602346 | 12/2005 |
| EP | 1704833 | 9/2006 |
| EP | 1719480 | 11/2006 |
| EP | 1754890 | 11/2006 |
| EP | 1736123 | 12/2006 |
| EP | 2074970 | 7/2009 |
| EP | 2074971 | 7/2009 |
| EP | 2087862 | 8/2009 |
| EP | 2095796 | 9/2009 |
| EP | 2095798 | 9/2009 |
| FR | 2797181 | 2/2001 |
| FR | 2823663 | 10/2002 |
| FR | 2855744 | 12/2004 |
| FR | 2921822 | 4/2009 |
| JP | 2005-334658 | 12/2005 |
| WO | WO 89/11701 | 11/1989 |
| WO | WO 00/09047 | 2/2000 |
| WO | WO 00/09049 | 2/2000 |
| WO | WO 2000/09048 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/47575 | 7/2001 |
| WO | WO 01/49245 | 7/2001 |
| WO | WO 01/70131 | 9/2001 |
| WO | WO 02/26317 | 4/2002 |
| WO | WO 02/053093 | 7/2002 |
| WO | WO 02/065948 | 8/2002 |
| WO | WO 03/077191 | 9/2003 |
| WO | WO 03/105732 | 12/2003 |
| WO | WO 2004/014245 | 2/2004 |
| WO | WO 2004/019671 | 3/2004 |
| WO | WO 2005/007232 | 1/2005 |
| WO | WO 2005/009305 | 2/2005 |
| WO | WO 2005/087147 | 9/2005 |
| WO | WO 2005/094447 | 10/2005 |
| WO | WO 2006/083885 | 8/2006 |
| WO | WO 2006/108203 | 10/2006 |
| WO | WO 2008/109300 | 9/2008 |
| WO | WO 2009/132127 | 10/2009 |

OTHER PUBLICATIONS

"Innovative medical devices and implants," LGSP Medical futures, p. 5.
Corno et al.; "FloWatchTM in clipped and inclipped position," Interact Cardio Vase Thorac Surg 2002; 1:46-49.
BioEnterics Lap-Band Adjustable Gastric Banding System, Inamed Health, pub. Aug. 28, 2003 pp. 1-115.
Iverson et al.; "Recent Advances in Microscale Pumping Technologies: A Review and Evaluation"; Microfluid Nanofluid; vol. 5; pp. 145-174; Feb. 19, 2008.

* cited by examiner

PARE PIEZO POWER WITH ENERGY RECOVERY

RELATED APPLICATIONS

This application is a continuation in part of, and claims priority to and the benefit of U.S. patent application Ser. No. 12/859,196, entitled "POWER REGULATED IMPLANT" filed on Aug. 18, 2010, the entire disclosure of which is incorporated herein by reference.

FIELD

The present invention generally relates to medical systems and apparatus and uses thereof for treating obesity and/or obesity-related diseases, and more specifically, relates to systems and methods for energy recovery in a laparoscopically-placed gastric band operably coupled to a piezo actuator.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts the food's passage into a lower portion of the stomach. When the stoma is of an appropriate size that is restricted by a gastric band, the food held in the upper portion of the stomach provides a feeling of satiety or fullness that discourages overeating. Unlike gastric bypass procedures, gastric band apparatus are reversible and require no permanent modification to the gastrointestinal tract.

Over time, a stoma created by a gastric band may need adjustment in order to maintain an appropriate size, which is neither too restrictive nor too passive. Accordingly, prior art gastric band systems provide a subcutaneous fluid access port connected to an expandable or inflatable portion of the gastric band. By adding fluid to or removing fluid from the inflatable portion by means of a needle, such as a Huber needle inserted into the access port, the effective size of the gastric band can be adjusted to provide a tighter or looser constriction.

Non-invasive adjustment systems and methods have also been proposed to change the constriction of a gastric band, for example, without the use of a needle. Some of these systems utilize implantable pumps to perform the constriction changes. However, the system specifications for these pumps, such as small size, power dissipation, flow rate, back pressure, and magnetic resonance imaging, result in challenging constraints for pump implementation.

Thus, there continues to remain a need for more effective implantable pump systems for use with adjustable gastric bands, particularly such implantable pump systems with pumping capability that achieves the desired flow rate within other design parameters such as voltage and temperature.

Further, there is a need for more effective implantable pump systems for adjustable gastric bands that are energy efficient and are capable of being optimized based on various factors.

SUMMARY

Generally described herein are implantable pumping systems for implantable gastric banding systems driven by a piezoelectric element pump. The apparatus and systems described herein aid in facilitating obesity control and/or treating obesity-related diseases while being non-invasive once implanted.

In an embodiment, a device for controlling a pump in an implantable gastric banding system comprises a positive terminal of a power source coupled via a first switch to a piezoelectric actuator, and a negative terminal of the power source coupled via a second switch to the piezoelectric actuator. The piezoelectric actuator may be coupled to an inductor to facilitate charging and discharging the piezoelectric actuator. The device for controlling a pump in an implantable gastric banding system may further comprise a first circuit comprising a first diode, a third switch, the inductor, and the piezoelectric actuator. The piezoelectric actuator may be operable to facilitate moving a fluid between a reservoir and an implantable portion of a gastric band.

The device for controlling a pump in an implantable gastric banding system further comprises a second circuit comprising a second diode, a fourth switch, the inductor, and the piezoelectric actuator. The first diode and the second diode may comprise opposite operational orientations to facilitate discharging the piezoelectric actuator and to facilitate energy recovery in the implantable gastric banding system. The device for controlling a pump in an implantable gastric banding system further comprises a microcontroller operable to control the operation of at least one of the first switch, the second switch, the third switch, or the fourth switch, according to a dynamic algorithm to optimize the energy recovery of the implantable gastric banding system. The dynamic algorithm may compensate for at least one of the uniqueness of each system component or aging of the devices in the system.

Further, in various embodiments, the system for energy recovery comprises at least one of a low voltage power supply, a high voltage power supply, an H bridge circuit, a sensor, or a power supply such as a battery. Additionally, a microcontroller may be configured to control the operation of at least one of the first switch or the second switch.

In accordance with an embodiment, the inductance value of the inductor is selected based on at least one of the piezoelectric actuator operating period or the current output of the piezoelectric actuator. Further, the piezoelectric actuator may operate below the piezoelectric actuator resonant frequency. For example, the piezoelectric actuator may operate below about 50 KHz.

Additionally, in various embodiments, a system for energy recovery in an implantable gastric banding system comprises a piezoelectric actuator for moving a fluid from a reservoir to an inflatable portion of a gastric band. A power supply is coupled to a terminal of the piezoelectric actuator, and an energy recovery device coupled to the terminal of the piezoelectric actuator. The system further comprises a first diode with a first orientation, and a first switch coupled to the first diode. A second switch is coupled to a second diode having a second orientation, and the second orientation is opposite the first orientation of the first diode.

In various embodiments, the energy recovery device is coupled to a first diode terminal of the first diode and a second diode terminal of the second diode to facilitate recharging of the piezoelectric actuator. The recharging may occur in response to at least one of the first switch or the second switch being closed. In various embodiments, the energy recovery device comprises at least one of an inductor or a capacitor.

Further, in accordance with an embodiment, a method for recovering energy from a piezoelectric actuator in an implantable gastric banding system comprises charging a piezoelectric actuator with a first magnitude of voltage of a first polarity from a power supply. The piezoelectric actuator may respond to the first magnitude of voltage to move a fluid from a reservoir to an inflatable portion of a gastric band of the implantable gastric banding system. The method for recovering energy may comprise discharging a flow of current of a first polarity from the piezoelectric actuator through an inductor coupled to a first diode comprising a first orientation. The flow of current may be discharged in response to closing a first switch coupled to the first diode, and the first switch may disconnect in response to a control signal being provided by a microcontroller.

The method for recovering energy may further comprise recharging the piezoelectric actuator with a second magnitude of voltage of a second polarity from the inductor. The second polarity may be an opposite polarity from the first polarity. The method for recovering energy may comprise recharging the piezoelectric actuator with a third magnitude of voltage of the second polarity from the power supply. The method for recovering energy may comprise discharging a flow of current of the second polarity from the piezoelectric actuator through the inductor coupled to a second diode having a second orientation opposite the orientation of the first diode, and the discharging may occur in response to the closing of a second switch coupled to the second diode. The second switch may disconnect in response to a control signal provided by the microcontroller.

Additionally, the method for recovering energy may comprise recharging the piezoelectric actuator with a fourth magnitude of voltage of the first polarity from the inductor. The method for recovering energy may comprise recharging the piezoelectric actuator with a fifth magnitude of the first polarity of voltage from the power supply. In various embodiments, the microcontroller is programmed with a dynamic algorithm. The dynamic algorithm may optimize operation of the system or compensate for at least one of the uniqueness of each system component or aging of the devices in the system. The dynamic algorithm may be implemented using software, hardware, or combinations thereof.

In an embodiment, a system for energy recovery in an implantable gastric banding system is disclosed. The system for energy recovery comprises a piezoelectric actuator coupled to an inductor to facilitate charging and discharging of the piezoelectric actuator. The system for energy recovery further comprises a first circuit comprising a first diode, a first switch, the inductor, and the piezoelectric actuator. The piezoelectric actuator is operable to facilitate moving a fluid between a reservoir and an implantable portion of a gastric band. The system for energy recovery further comprises a second circuit comprising a second diode, a second switch, the inductor, and the piezoelectric actuator. The first diode and the second diode comprise opposite operational orientations to facilitate discharging the piezoelectric actuator and to facilitate energy recovery in the implantable gastric banding system.

DETAILED DESCRIPTION

The present invention generally provides remotely adjustable gastric banding systems, for example, for treatment of obesity and obesity related conditions, as well as systems for controlling inflation of gastric banding systems.

A remotely adjustable gastric band is a medical device which allows a healthcare worker to adjust a gastric band without utilizing needles to connect to an implanted access port. An external, handheld controller may be used to send radio frequency signals for powering and communicating with the implanted device. The implanted device may fill or drain the gastric band as requested by the healthcare worker via the handheld controller. The handheld controller may be a remote device configured to produce a telemetric signal that controls the various components of the gastric banding system.

In various embodiments of the present invention, the filling and draining of the band is accomplished by a set of fluidic elements including pumps, valves, and sensors which monitor and/or move fluid between the gastric band and a reservoir. In accordance with various embodiments, different numbers, types, and orientations of the fluidic elements may be utilized to obtain the desired results. Any and/or all of these various components may be configured to be controlled by a remote transmitter, such as a handheld controller.

For example, an implantable pump may be utilized to move the fluid through the adjustable gastric banding system. Considerations involved with the implantable pump include size, power dissipation, maintenance requirements, precision of operation, flow rate, back pressure, and effects on magnetic resonance imaging. Various embodiments of the present invention provide adjustable gastric banding systems that achieve the appropriate specifications for these and other considerations.

Figure 1:
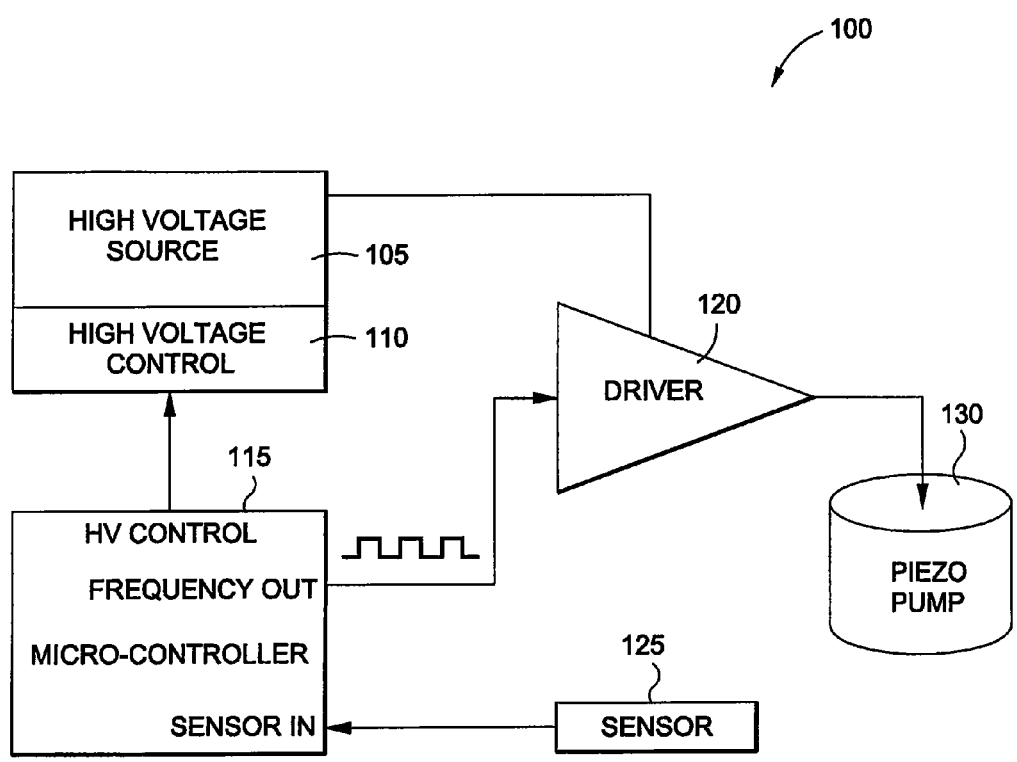
FIG. 1 illustrates a schematic view of an implantable pumping system according to an embodiment of the present invention.

Turning now to FIG. 1, an implantable pumping system 100, according to an embodiment, comprises a piezo actuator based pump 130. A voltage source, such as a high voltage source 105 is utilized to polarize the piezo actuators in the pump 130. A voltage control circuit, such as a high voltage control circuit 110 is configured to increase or decrease the magnitude of the voltage. In various embodiments, the voltage may be in the range of approximately 20 volts to approximately 300 volts. In an embodiment, the piezoelectric actuator may operate below about 50 KHz. The piezoelectric actuator element displacement may be between about a nanometer and about a millimeter.

In one embodiment, the piezo static capacitance is about 48 nF. In such an embodiment, the piezo actuator may be driven by a square wave with a 10 mS period, and an effective drive voltage of 210 volts. Components may be selected based on their size, cost, resistance, and ease of integration.

Figure 2A:
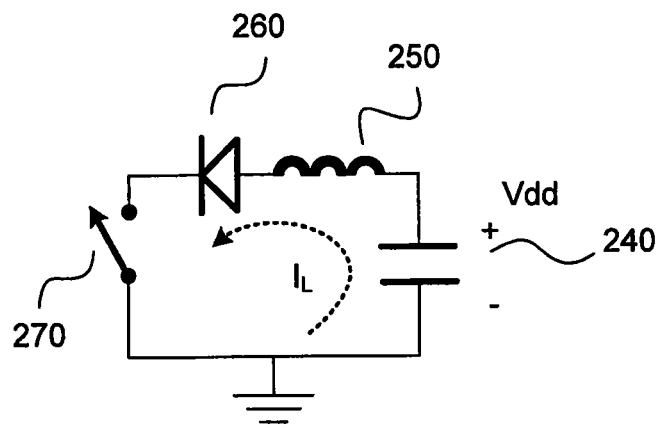
FIG. 2a illustrates a simplified circuit diagram according to an embodiment of the present invention.

With reference to FIG. 2a, a piezo actuator 240 associated with the piezoelectric actuator based pump 130 is depicted. When driven by a periodic voltage source at a frequency below the resonant frequency of the piezoelectric actuator 240, the equivalent circuit model for the piezoelectric actuator 240 may be simplified to a single capacitor resulting in the equation:

$$P=CV^2F \quad (1)$$

Where the power (P) is determined by the product of the capacitance (C), the square of the voltage (V), and the driving frequency (F). The voltage, piezo capacitance (which is generally related to the actuator size), and driving frequency may not be capable of being reduced without adversely impacting proper operation of the piezoelectric actuator 240. However, since the piezoelectric actuator 240 functionally operates as an energy storage device, energy may be recovered to reduce required power. Thus, references to a piezoelectric actuator or a piezo actuator encompass a piezoelectric actuator capacitance.

Power dissipation due to charging and discharging the piezo actuator 240 may be significant. The charging of an initially discharged capacitance, C, from a constant voltage source, V, requires a total energy, E, expressed by the equation:

$$E=C*V^2 \quad (2)$$

Upon fully charging the piezo actuator 240, the energy stored in the capacitor may be half ($\frac{1}{2}*C*V^2$) the total energy where the other half of the energy may be dissipated in the circuit resistance. In one embodiment, after discharging, the piezo actuator's 240 stored energy may be dissipated in the circuit resistance. Stated another way, the energy put into the circuit is dissipated as heat and not as the useful work of piezo actuator 240 motion.

In one embodiment, the energy stored in the piezo actuator 240 may be recovered, instead of being transferred into heat in the circuit resistance. Recovering the stored energy may lower the power input to the circuit from a power supply. In various embodiments, two types of electronic passive energy storage devices that may be utilized are (1) a capacitor and (2) an inductor. These devices may be used for energy recovery, alone or in combination.

For example, in one embodiment, the charge stored in the piezo actuator 240 may be transferred to a second recovery capacitor during discharge of the piezo actuator 240. Subsequently, such as on the next charge cycle of the piezo actuator 240, the recovery capacitor may provide its stored energy back to the circuit. In another example, the resonance between a recovery inductor 250 and the piezo actuator 240 provides a mechanism for theoretically recovering substantially all of the energy of the piezo actuator 240.

The interaction of the inductor with other medical devices, such as interaction with magnetic resonance imaging devices, may be a factor in determining selection of passive energy storage devices. For instance, an inductor may have a composition that will interact with a magnetic field which may create undesirable results. Thus, a capacitor selection over an inductor may be justified considering constraints of an MRI environment.

With reference again to FIG. 2a and FIG. 2b, and according to various embodiments, a diode 260, a recovery inductor 250, a piezo actuator 240, and a switch 270 are illustrated. In one embodiment, for t<0 the capacitance C of the piezo actuator 240 modeled as a capacitor is initially charged to voltage Vdd and no current is flowing in the circuit since the switch 270 is open. At t=0 the switch 270 is closed and current will start flowing from the piezo actuator 240 in the direction shown by the arrow. Under these conditions the diode 260 is considered an ideal short circuit. As current $I_L$ flows, a magnetic field is induced in the recovery inductor 250 until the piezo actuator 240 is substantially fully discharged at Vc=0V. In response to the piezo actuator 240 being substantially fully discharged, the current in the recovery inductor 250 ramps down or is reduced as the magnetic field of the recovery inductor 250 collapses and, in the process, energy from the magnetic field is transferred back to the piezo actuator 240. This process continues until the magnetic field has substantially fully dissipated and the piezo actuator 240 has been charged to −Vdd. Repeating or oscillating cycles do not occur due to the operation of diode 260. The diode 260 may be considered an ideal open circuit completing one cycle of energy transfer.

Figure 2B:
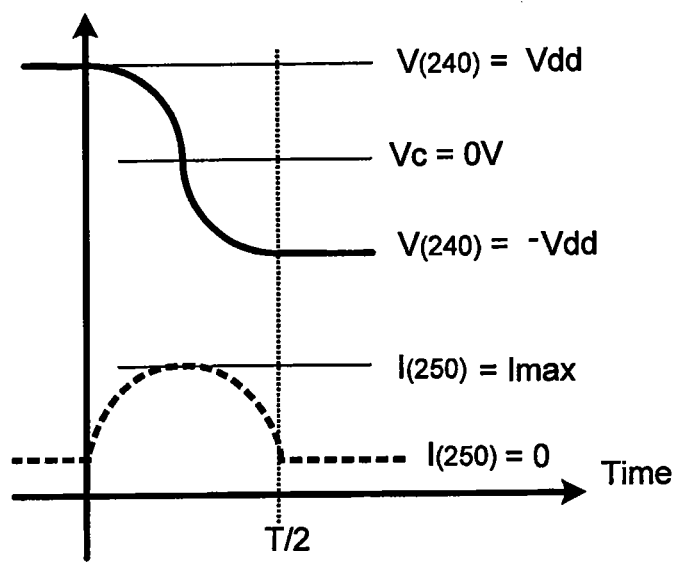
FIG. 2b illustrates the ideal voltage across the piezo electric actuator capacitive element (Vc) and the ideal current through the inductor of FIG. 2a according to an embodiment of the present invention.

With renewed reference to FIG. 2b, and in accordance with an embodiment, the cycle for the recovery inductor 250 current and piezo actuator 240 voltage is depicted. The period of current flow in the circuit may be expressed as:

$$T/2=1/(2*Freq)=\pi*(L*C)^{1/2} \quad (3)$$

In an embodiment, the switch 270 is controlled in response to the algorithm programmed into a microcontroller 420 coupled to the system. In response to advantageously configured timing, when substantially full energy is transferred to the piezo actuator 240, the algorithm directs the microcontroller to send a signal to the switch 270 to open. The operation of the microcontroller will be further discussed below. In one embodiment, switch 270 may automatically open when the substantially full energy transfer to the piezo actuator 240 occurs.

Further, in one embodiment, losses due to resistance in the components, and non-ideal components may alter the previously presented equations. A power supply may be employed to inject power into the system to compensate for losses. Also, the power supply may be implemented to hold a voltage on the capacitance for substantially the full +Vdd to −Vdd voltage swing. The magnitude of the power transferred from the power supply may be proportional to and based on the loss in the circuit.

Figure 3:
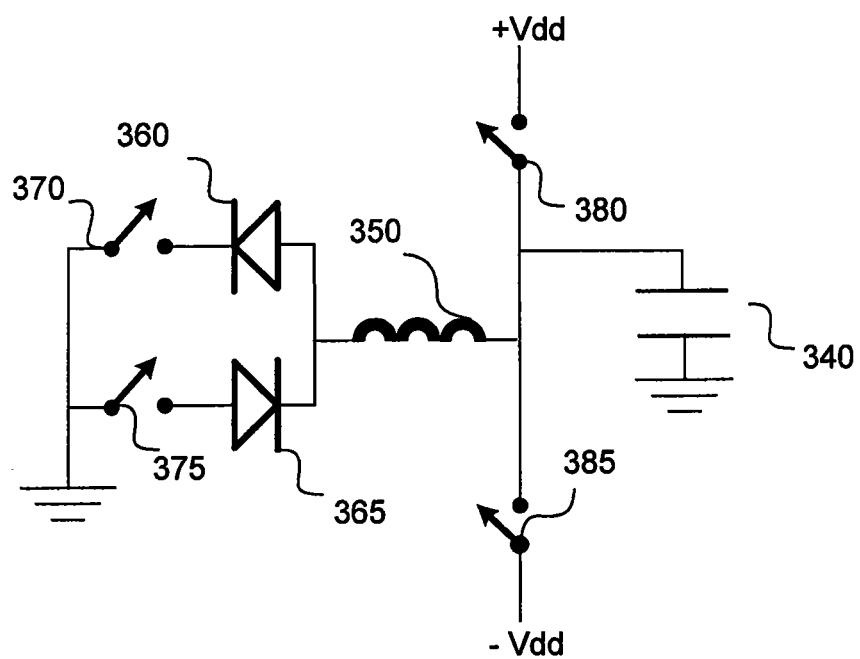
FIG. 3 illustrates a simplified circuit diagram according to another embodiment of the present invention.

In one embodiment, a simplified practical circuit for a repeating cycle of charging and discharging the piezo actuator 340 capacitance is shown in FIG. 3. For example, charging the piezo actuator 340 capacitance to a positive or negative Vdd may be accomplished with opposite diode 360, 365 orientations and using a shared recovery inductor 350. The inductance value may be selected based on saturation point of the recovery inductor 350 relative to the full current of the piezo actuator 340 capacitance. Also, the inductance value may be selected so that time T/2 from the above equation is less than half the piezo actuator 340 operating period. The switches 370, 375, 380, and 385 may be any suitable switch, such as a field effect transistor (FET), a bipolar junction transistor (BJT), (MOSFET), (HFET), (MESFET) and/or the like.

Figure 4:
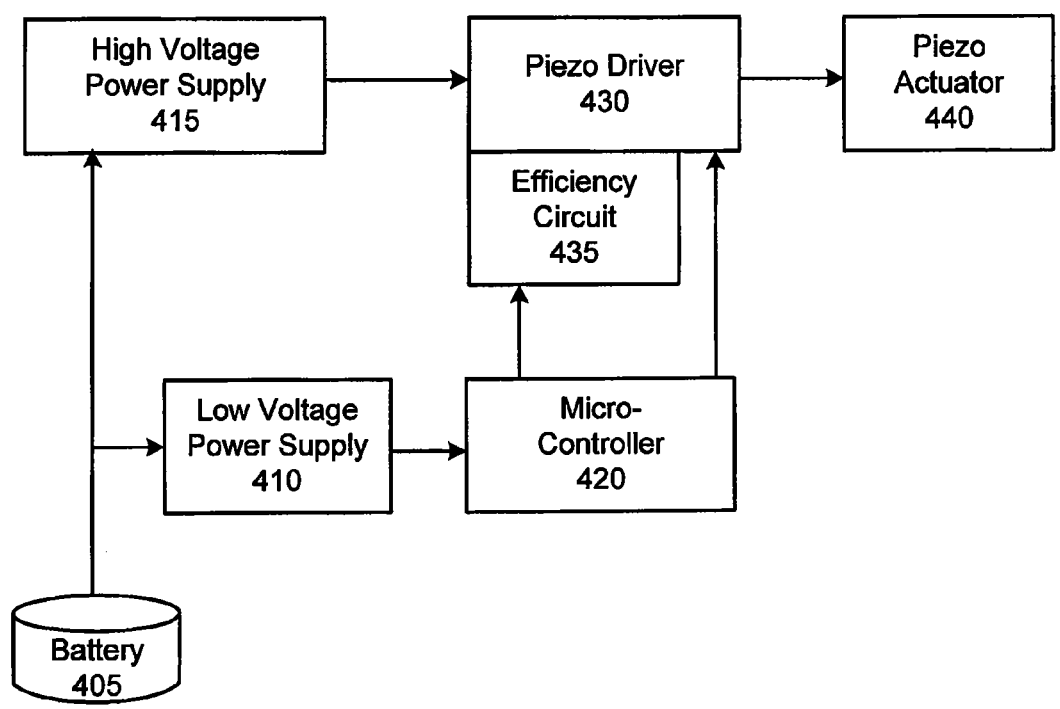
FIG. 4 illustrates the functional blocks for a battery operated piezo actuator circuit according to an embodiment of the present invention.

With reference to FIG. 4, a diagram indicating the functional blocks for a piezo actuator 440 circuit is illustrated according to an embodiment of the present invention. In this embodiment, the power source is a DC battery 405. Also, in various embodiments, a backup and/or a second battery may be coupled to the system. A low voltage power supply 410 may regulate the battery 405 to a specified voltage for the microcontroller 420 in the circuit. The low voltage supply 410 may be a linear regulator, a buck or boost switching regulator based on the battery 405 voltage. The high voltage supply 415 may generate the piezo actuator 440 electric field. The piezo actuator 440 electric field may be implemented with a boost topology switching regulator.

In one embodiment, the microcontroller 420 may include a memory unit for storing the algorithms described herein. The microcontroller 420 and/or a processor may be used to execute the algorithms described herein. Other devices described herein may also be used to execute and/or store the algorithms described herein.

In various embodiments, the microcontroller 420 may be any suitable microcontroller. The microcontroller 420 may be selected based on it being a low power device capable of generating the piezo actuator 440 operating frequency and providing control signals for the piezo driver 430 and efficiency circuit 435. The piezo driver 430 may be configured to apply a voltage to the piezo actuator 440 with a proper phase and frequency. In various embodiments, the frequency may be in the range of approximately 10 Hz to approximately 1,000 Hz. Further, in various embodiments, the voltage applied to the pump 130 by the driver 120 may be in the range of approximately 20 volts to approximately 300 volts.

Figure 5:
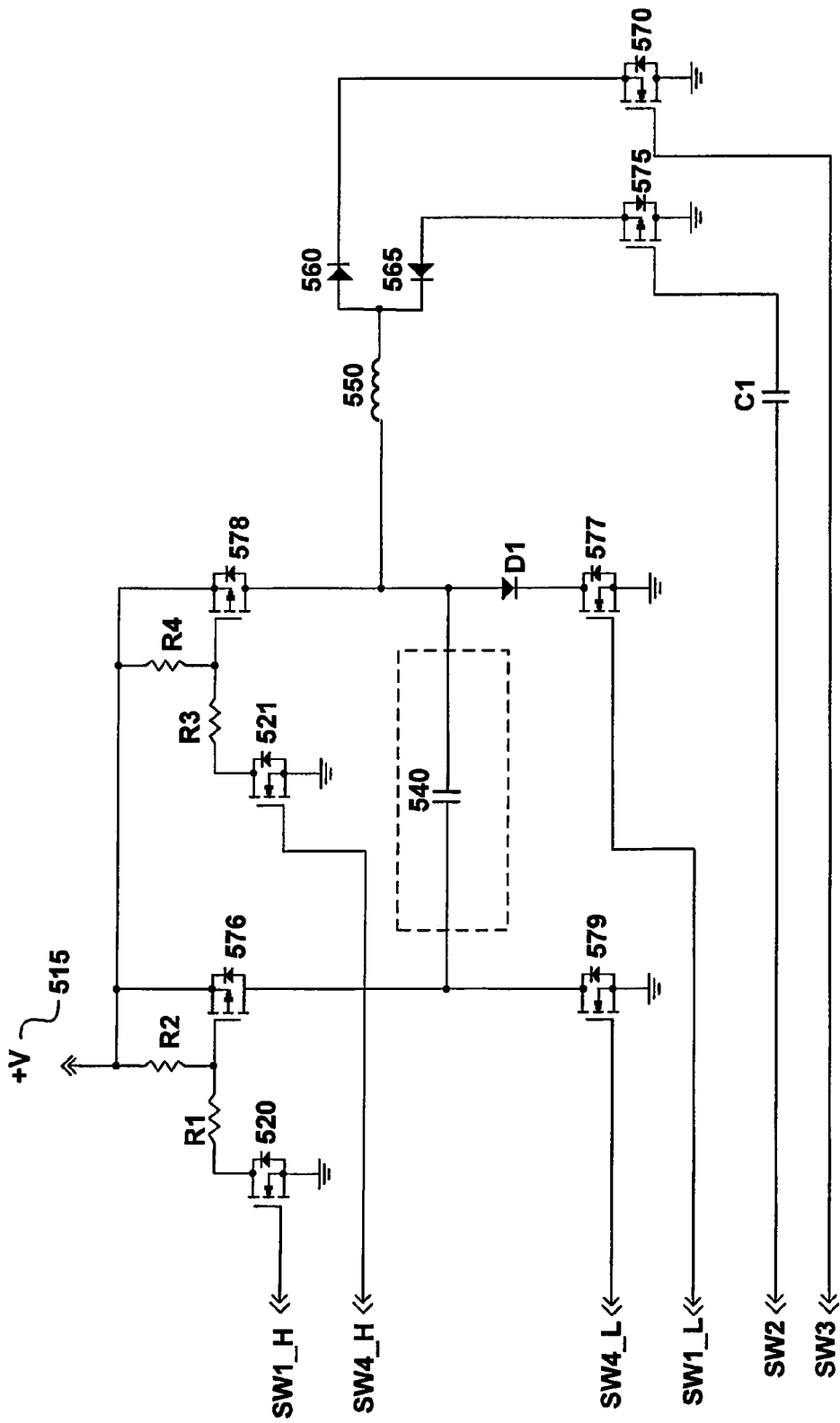
FIG. 5 illustrates a circuit diagram according to an embodiment of the present invention.

With reference to FIG. 5, and in accordance with an embodiment, the simplified circuit depicted in FIG. 3 is illustrated in more detail as implementing an H-bridge driver along with FETs 570, 575, 576, 577, 578, 579, 520, and 521 to represent switches 370, 375, 380 and 385 from FIG. 3. The H-bridge may support the use of a single high voltage source 515 to oppositely polarize the piezo actuator 540 during each half of the operating period. In particular, the switch 380 of FIG. 3 is represented by the current path enabled when the FET 578 and the FET 579 are on, while the switch 385 of FIG. 3 is represented by the current path enabled when the FET 576 and the FET 577 are on.

Though any suitable level translators may be utilized, R1, R2, and FET 520 are implemented as level translators interfacing between the high voltage associated with the FET 576 and the low voltage output of the microcontroller 420. Similarly, R3, R4 and FET 521 may be implemented as level translators interfacing between the high voltage associated with the FET 578 and the low voltage output of the microcontroller 420.

Figure 6:
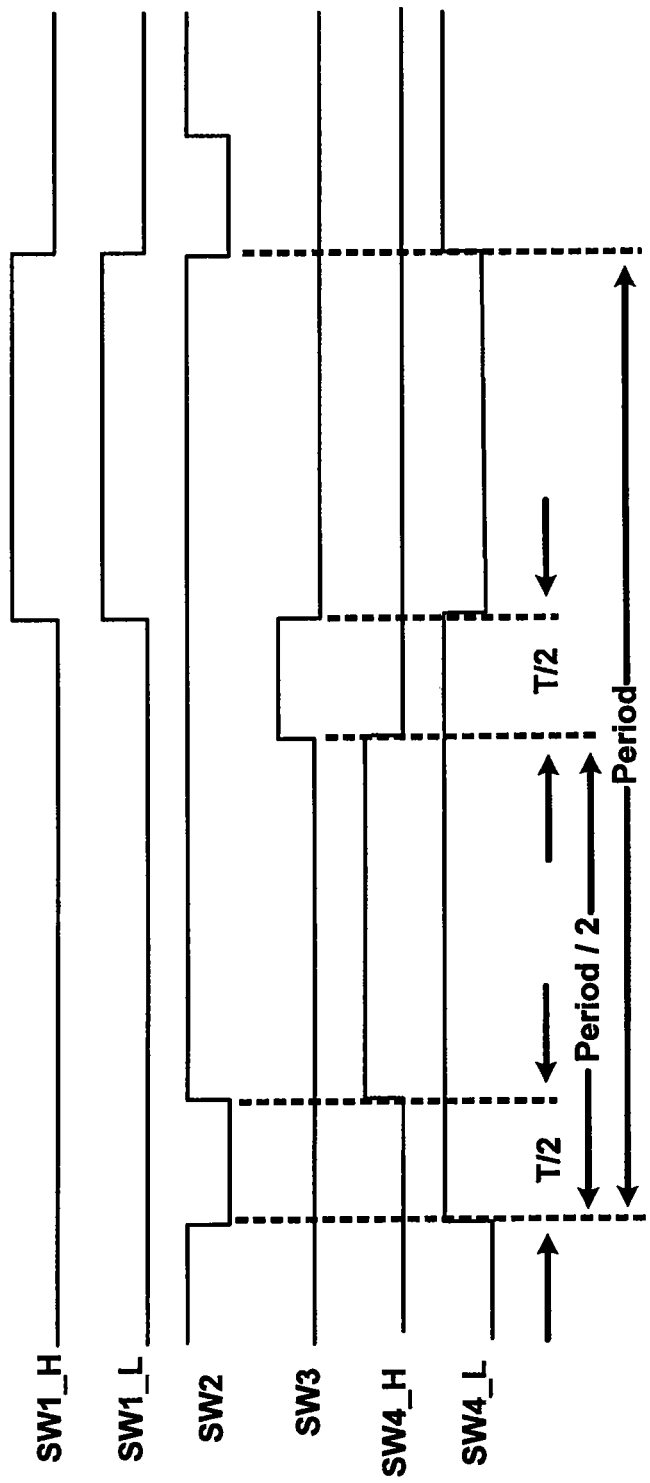
FIG. 6 depicts an exemplary timing diagram of the microcontroller according to an embodiment of the present invention.

A diode D1 may be utilized to prevent the piezo actuator 540 from discharging through the FET 577 instead of the intended path through the recovery inductor 550, the diode 565, and the FET 575. A capacitor C1 provides translation of a low going signal on SW2 to a negative voltage to turn on the FET 575. In an embodiment, the microcontroller orchestrates the control for each of the FETs 570, 575, 577, 579, 520, and 521 gate signals to produce the sequence illustrated in FIG. 6.

Figure 7:
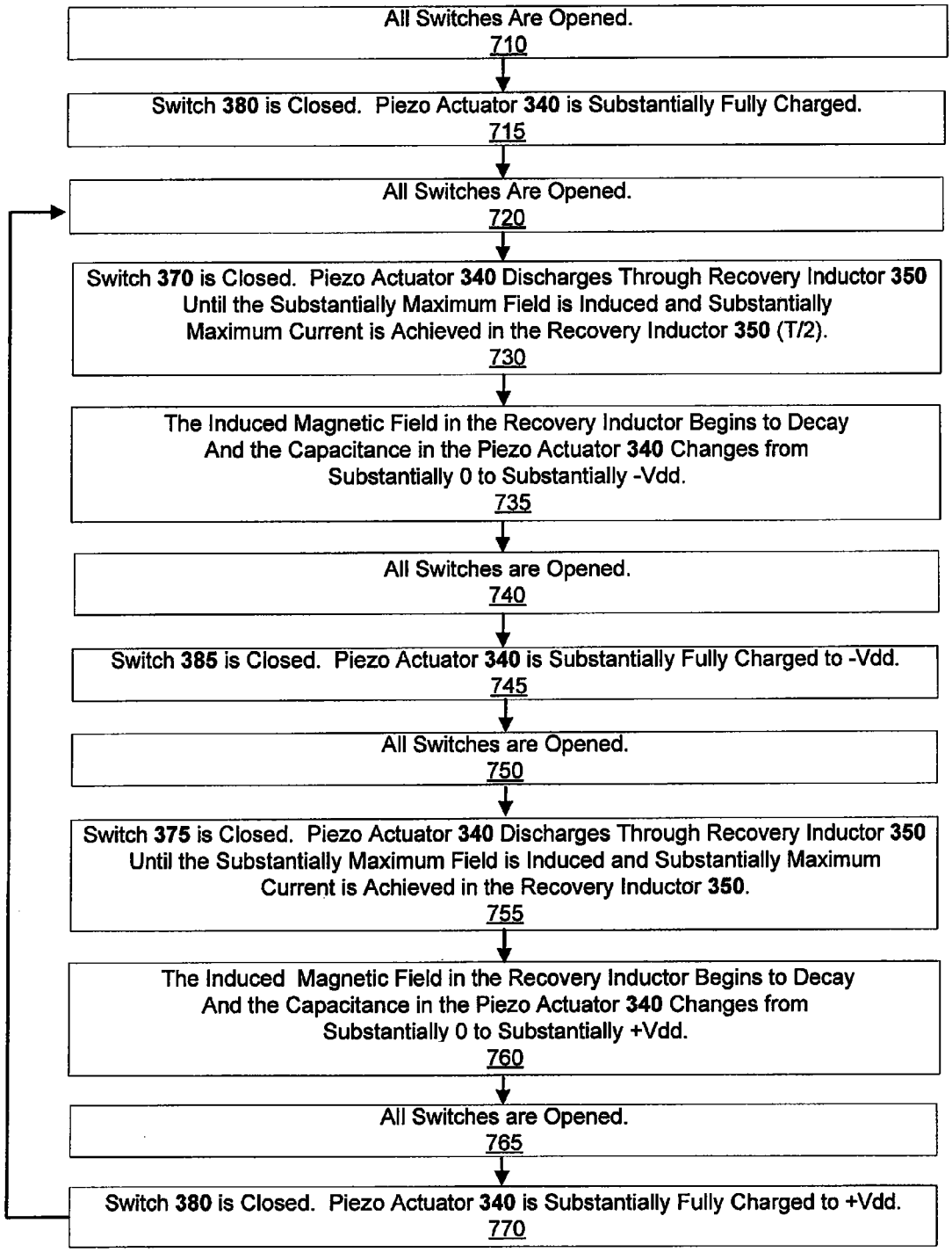
FIG. 7 illustrates a flow chart representing a method of energy recovery according to an embodiment of the present invention.

Further, in one embodiment, and with reference to FIG. 7, a method of operation of the switches and/or FETs is depicted. For simplicity, the switches depicted in FIG. 3 are referenced. The microcontroller 420 and a dynamic algorithm associated therewith controls the operation of the switches and/or the FETs.

At T=0, all switches are open (710). Subsequently, switch 380 is closed. At this point, the piezo actuator 340 is substantially fully charged via a terminal of the power source, such as the +Vdd terminal of the power source (715).

All switches are then opened (720). Subsequently, switch 370 is closed, creating a complete electrical circuit from the piezo actuator 340 through the recovery inductor 350, the diode 360, and the switch 370 to ground (730). Resonance is created between the recovery inductor 350 and the piezo actuator 340, thus reversing the polarity of the capacitive load from +Vdd to −Vdd. In one embodiment, a voltage equal to or a voltage between +Vdd to −Vdd may be represented as a first magnitude, second magnitude, third magnitude, fourth magnitude and fifth magnitude of voltage having a positive or negative polarity. Energy is initially stored in the recovery inductor 350 and then returned to the piezo actuator 340 with reversed polarity.

A magnetic field is induced in the recovery inductor 350 due to the current passing through it. At T/4 the current is at a maximum. After T/4, the induced magnetic field begins to decay. At T/2 the polarity of the voltage in the capacitor is substantially reversed to −Vdd (735).

All switches are then opened (740). Subsequently, switch 385 is closed and the piezo actuator 340 is substantially fully charged via a terminal of the power source, such as the −Vdd terminal of the power source to compensate for losses of the system (745).

All switches are opened again (750). Subsequently, switch 375 is closed, creating a complete electrical circuit from the piezo actuator 340 through the recovery inductor 350, the diode 365, and the switch 375 to ground (755). Resonance is again created between the recovery inductor 350 and the piezo actuator 340, thus reversing the polarity of the capacitive load from −Vdd to +Vdd (760).

Again, all switches are then opened (765). Subsequently, switch 380 is closed and the piezo actuator 340 is substantially fully charged via a terminal of the power source due to losses of the system (770). This process may continue as desired. Although the method is described as initially putting a +Vdd polarity on the piezo actuator 340, it is understood that a −Vdd polarity could be used in the alternative.

In one embodiment, an algorithm controlling operation of the microcontroller may optimize the timing of the opening and closing of the switches in the system. For instance, minimizing the time between steps 740 and 745 may result in efficiencies. Also, determining T/2 and/or T/4 with increased precision may result in operational efficiencies of the system.

This algorithm may be dynamic. As components of the system, such as the piezo actuator 340, the recovery inductor 350, the diodes or switches age, the timing of their operation may change. Alternatively, components may have different operational tendencies due to manufacturing irregularities and/or other material defects. The algorithm may be dynamically updated by self optimization to account for these changes in operation. Adding feedback, such as a power monitor, to the implementation previously described can provide further advantage for reducing the piezo pump power. In particular, variations in the piezo actuator due to manufacturing tolerances, aging, or applied voltage can be compensated by the algorithm of the micro-controller 420 that periodically adjusts the timing of the piezo actuator control waveforms to minimize the measured circuit power.

Figure 8:
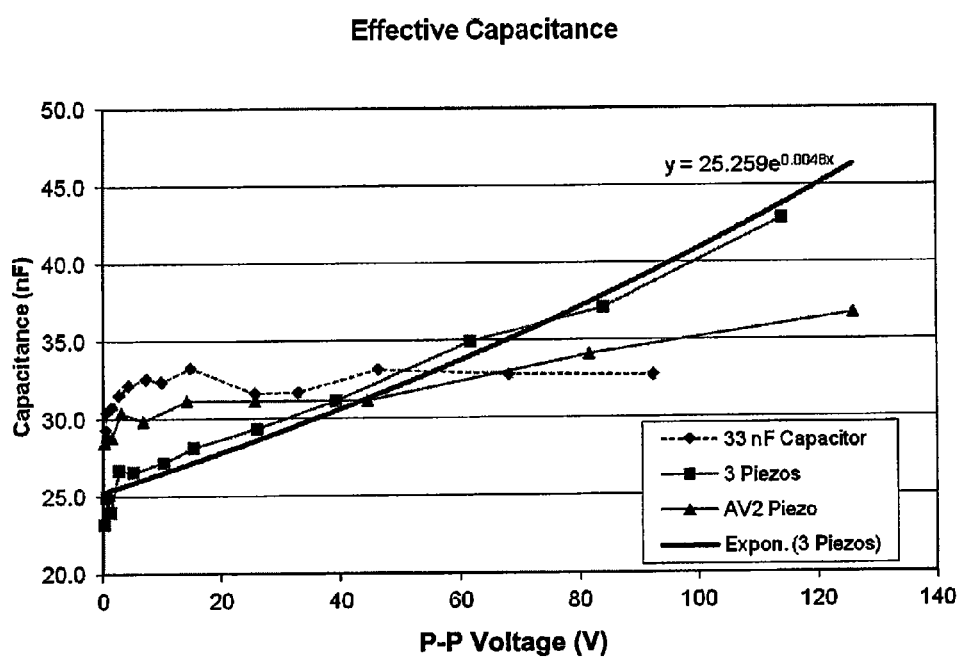
FIG. 8 depicts an exemplary embodiment of effective capacitance variation due to applied voltage according to an embodiment of the present invention.

An example of variation due to applied voltage is shown in FIG. 8. The power monitor, such as a sensor, may be implemented by measuring current into the piezo driver circuit, or by measuring other related parameters, such as a suitable voltage or temperature. Based on the feedback, the efficiency circuit 435 may adjust timing of the microcontroller 420 control signals to the switches to achieve greater operational efficiency and energy recovery.

Figures 9, 9A:
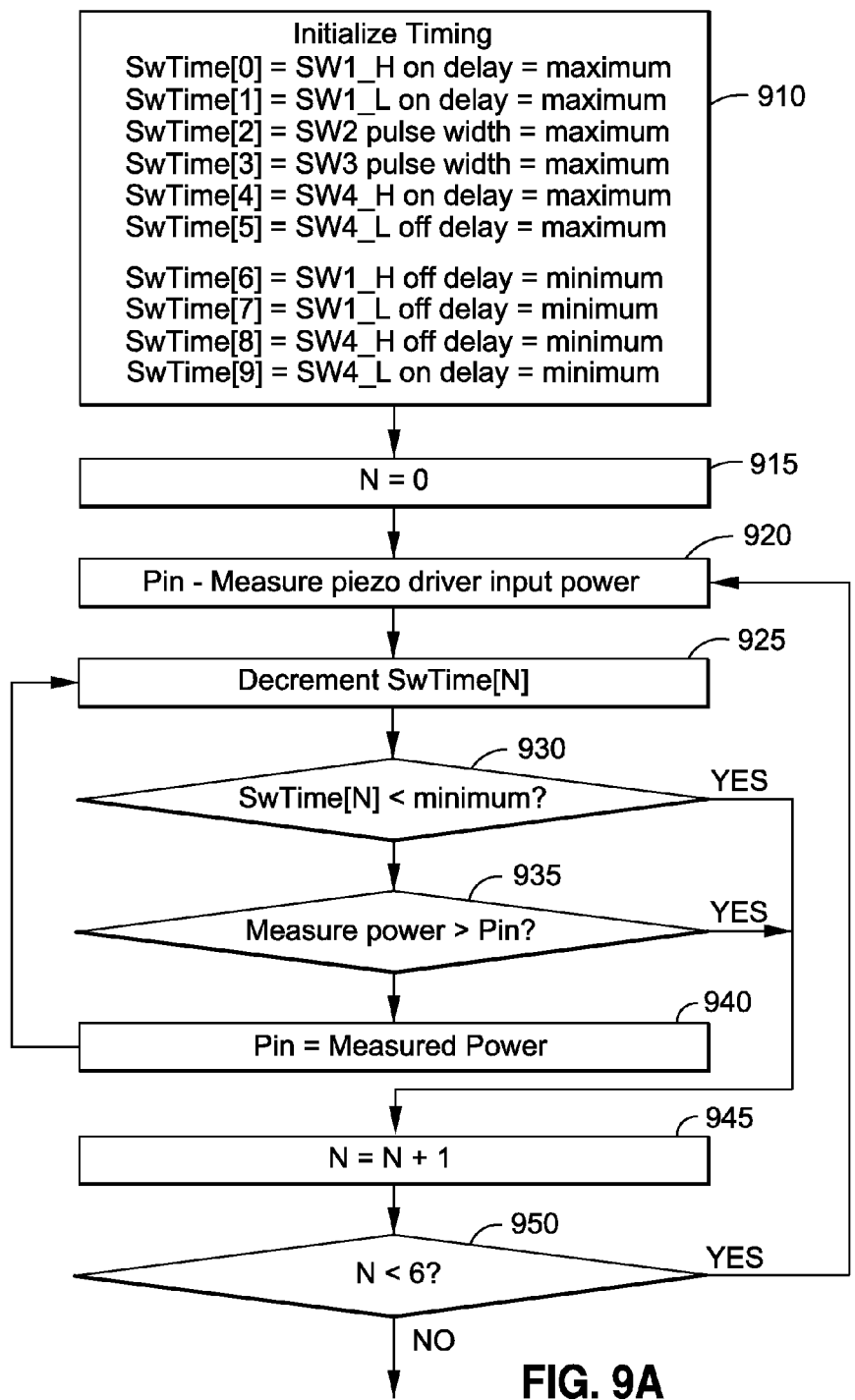
FIG. 9 illustrates a flow chart representing a method of adjusting the timing of the piezo actuator control waveforms to minimize power according to an embodiment of the present invention.
Figure 9B:
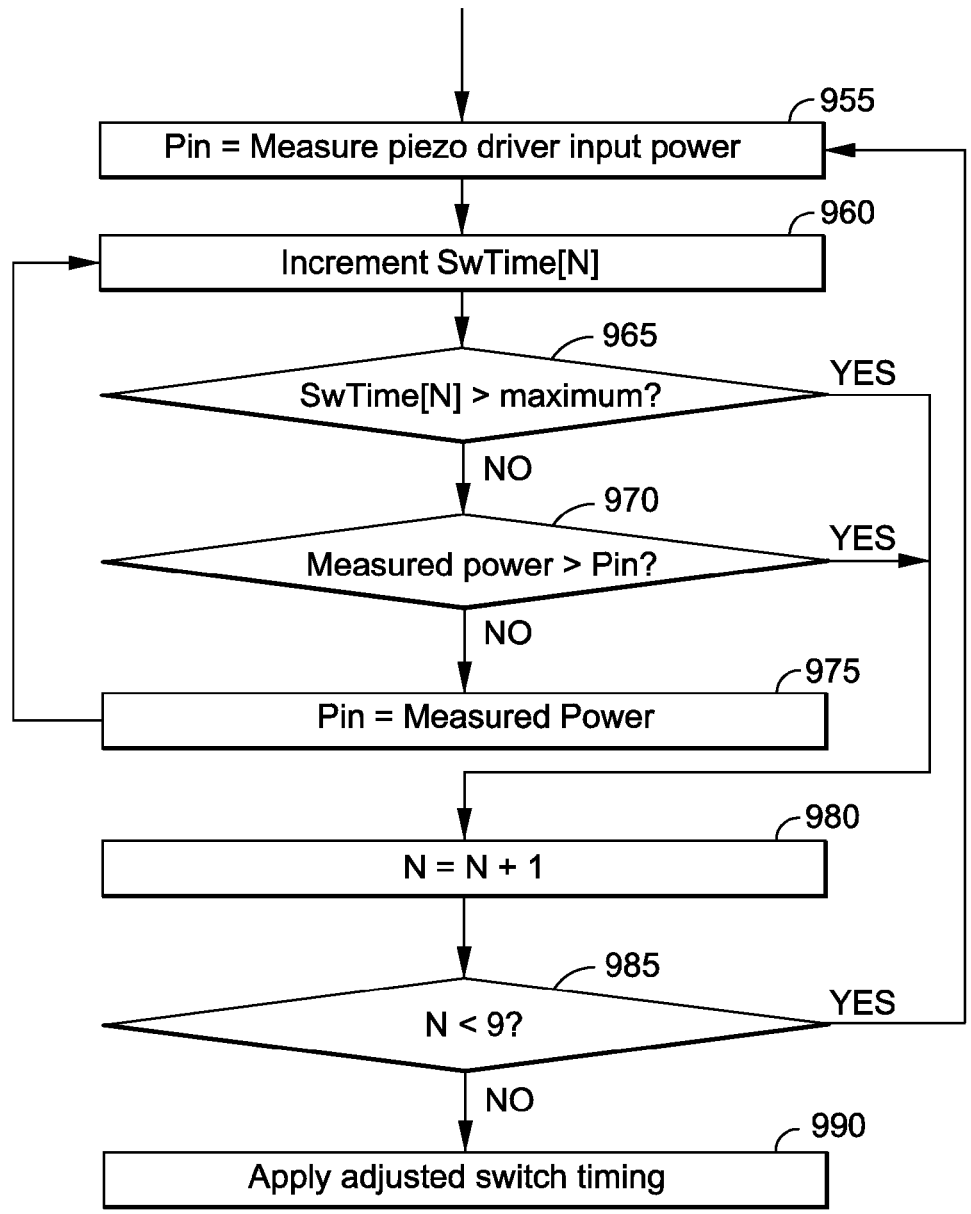

With reference to FIG. 9, and in accordance with an embodiment, a method for self-adjusting the timing of the control waveforms of the system to minimize power is illustrated. At the outset, the switch timing is formatted and initialized to established conditions (910). SwTime[N] is set to 0 (915). A measurement of the piezo driver input power is then taken (920).

Next, a feedback loop is implemented to determine the minimum timing of switches 370, 375, 380, and 385 by comparing the preset or previous timing and/or preset or previous measured piezo driver input power to the current measured timing and piezo driver input power (915, 920, 925, 930, 935, 940, 945, 950). For instance, the minimum pulse width of switches 370, 375, the minimum on delays of the switch 385 and the minimum on delay of the positive terminal of the switch 380 are determined. Also, the minimum off delay of the negative terminal of switch 380 is determined.

Again, a feedback loop is implemented to determine the maximum timing of the switches 380 and 385. For instance, the maximum off delays of the switch 385 and the maximum off delay of the positive terminal of the switch 380 are determined. Also, the maximum on delay of the negative terminal of the switch 380 is determined (955, 960, 965, 970, 975, 980, 985). In response to the maximums and minimums of the switches 370, 375, 380, and 385 being determined, the findings are applied and the switch timing in the microcontroller 420 is adjusted (990).

In one embodiment, a multi-piezo element pump may be implemented, such as a pump comprising multiple piezo elements within a single housing. For example, a 6 element piezo pump may be utilized in connection with a piezoelectric diaphragm and passive check valves to move fluid from a reservoir to a first pump chamber and then to a second pump chamber. A piezo actuator element mounted on a membrane may be deformed when voltage is applied. By the resulting downstroke associated with the deformation, the medium may be displaced out of the first pump chamber to a second pump chamber. When the voltage decreases, the corresponding deformation of the piezo element causes an upstroke of the membrane. This upstroke results in the first pump chamber being filled again. In some embodiments, check valves on both sides of the pump chamber may define the flow direction. In other embodiments, the elasticity of the system may cause the medium to flow in one direction while the pump is utilized to transfer medium in the opposite direction.

Unless otherwise indicated, all numbers expressing quantities of ingredients, volumes of fluids, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. For instance, reference to a recovery inductor may be substituted with a recovery capacitor throughout. Accordingly, the present invention is not limited to that precisely as shown and described.

What is claimed is:

1. A device for controlling a pump in an implantable gastric banding system, the device comprising:
   a positive terminal of a power source coupled via a first switch to a piezoelectric actuator;

a negative terminal of the power source coupled via a second switch to the piezoelectric actuator, wherein the piezoelectric actuator is coupled to an inductor to facilitate charging and discharging the piezoelectric actuator;

a first circuit comprising a first diode, a third switch, the inductor, and the piezoelectric actuator, wherein the piezoelectric actuator is operable to facilitate moving a fluid between a reservoir and an inflatable portion of a gastric band;

a second circuit comprising a second diode, a fourth switch, the inductor, and the piezoelectric actuator, wherein the first diode and the second diode comprise opposite operational orientations to facilitate discharging the piezoelectric actuator and to facilitate energy recovery in the implantable gastric banding system; and a microcontroller operable to control the operation of at least one of the first switch, the second switch, the third switch, or the fourth switch, according to a dynamic algorithm to optimize the energy recovery of the implantable gastric banding system.

2. The device of claim 1, wherein the dynamic algorithm compensates for at least one of the uniqueness of each system component or aging of the devices in the system.

3. The device of claim 1, wherein the power source further comprises a low voltage power supply and a high voltage power supply.

4. The device of claim 3, wherein the low voltage power supply comprises at least one of a linear regulator, a buck switching regulator, or a boost switching regulator.

5. The device of claim 1, wherein a substantial maximum inductance value of the inductor is selected based on an operating period of the piezoelectric actuator.

6. The device of claim 1, wherein the piezoelectric actuator operates below a resonant frequency of the piezoelectric actuator.

7. The device of claim 1, wherein the piezoelectric actuator operates below about 50 KHz.

8. The device of claim 1, wherein the substantial minimum inductance value of the inductor is selected based on a current output of the piezoelectric actuator.

9. The device of claim 1, wherein the power supply comprises a battery.

10. The device of claim 1, wherein the system comprises an H bridge circuit.

11. The device of claim 1, wherein at least one of the first switch or the second switch comprises a field effect transistor.

12. The device of claim 1, further comprising a sensor for measuring a power value.

13. A system for energy recovery in an implantable gastric banding system, comprising:

a piezoelectric actuator for moving a fluid from a reservoir to an inflatable portion of a gastric band;

a power supply coupled to a terminal of the piezoelectric actuator;

an energy recovery device coupled to the terminal of the piezoelectric actuator;

a first diode;

a first switch coupled to the first diode having a first orientation;

a second switch; and a second diode coupled to the second switch, wherein the second diode comprises a second orientation, and wherein the second orientation is opposite the first orientation of the first diode, wherein the energy recovery device is coupled to a first diode terminal of the first diode and a second diode terminal of the second diode to facilitate recharging the piezoelectric actuator in response to at least one of the first switch or the second switch being closed.

14. The system of claim 13, wherein the energy recovery device comprises at least one of an inductor or a capacitor.

15. A method for recovering energy from a piezoelectric actuator in an implantable gastric banding system, the method comprising:

charging a piezoelectric actuator with a first magnitude of voltage of a first polarity from a power supply, wherein the piezoelectric actuator responds to the first magnitude of voltage to move a fluid from a reservoir to an inflatable portion of a gastric band of the implantable gastric banding system;

discharging a flow of current of a first polarity from the piezoelectric actuator through an inductor coupled to a first diode having a first orientation in response to closing a first switch coupled to the first diode, wherein the first switch disconnects in response to a first control signal provided by a microcontroller;

recharging the piezoelectric actuator with a second magnitude of voltage of a second polarity from the inductor, wherein the second polarity is an opposite polarity from the first polarity;

recharging the piezoelectric actuator with a third magnitude of voltage of the second polarity from the power supply;

discharging a flow of current of the second polarity from the piezoelectric actuator through the inductor coupled to a second diode having a second orientation in response to the closing of a second switch coupled to the second diode, wherein the second switch disconnects in response to a second control signal provided by the microcontroller, and wherein the second orientation of the second diode is opposite the first orientation of the first diode;

recharging the piezoelectric actuator with a fourth magnitude of voltage of the first polarity from the inductor; and recharging the piezoelectric actuator with a fifth magnitude of voltage of the first polarity of voltage from the power supply.

16. The method of claim 15, wherein microcontroller is programmed with a dynamic algorithm, wherein the algorithm dynamically optimizes operation of the system to reduce power consumption.

17. The method of claim 16, wherein the dynamic algorithm compensates for at least one of the uniqueness of each system component or aging of the devices in the system.

18. A system for energy recovery in an implantable gastric banding system, the system for energy recovery comprising:

a piezoelectric actuator coupled to an inductor to facilitate charging and discharging the piezoelectric actuator;

a first circuit comprising a first diode, a first switch, the inductor, and the piezoelectric actuator, wherein the piezoelectric actuator is operable to facilitate moving a fluid between a reservoir and an implantable portion of a gastric band; and a second circuit comprising a second diode, a second switch, the inductor, and the piezoelectric actuator, wherein the first diode and the second diode comprise opposite operational orientations to facilitate discharging the piezoelectric actuator and to facilitate energy recovery in the implantable gastric banding system.

19. The system of claim 18, wherein a power supply is coupled to the system.

20. The system of claim 18, further comprising a microcontroller, wherein the microcontroller controls the operations of the first switch and the second switch.

* * * * *